United States Patent [19]

Deger et al.

[11] Patent Number: 5,763,701
[45] Date of Patent: Jun. 9, 1998

[54] PROCESS FOR PREPARING PENTAFLUOROETHANE (R 125)

[75] Inventors: Hans-Matthias Deger, Hofheim; Werner Krause, Hürth; Dieter Schmid, Schwalbach; Martin Hoeveler, Idstein, all of Germany

[73] Assignee: Solvay (Societe Anonyme), Belgium

[21] Appl. No.: 617,218

[22] Filed: Mar. 18, 1996

[30] Foreign Application Priority Data

Mar. 20, 1995 [DE] Germany ............... 195 10 024.7

[51] Int. Cl.$^6$ ........................... C07C 19/08
[52] U.S. Cl. ........................... 570/134
[58] Field of Search ........................... 570/134

[56] References Cited

U.S. PATENT DOCUMENTS

| | | |
|---|---|---|
| 3,258,500 | 6/1966 | Swamer et al. |
| 3,755,477 | 8/1973 | Firth et al. |
| 4,547,483 | 10/1985 | Müller et al. |
| 5,157,172 | 10/1992 | Wanzke et al. |

FOREIGN PATENT DOCUMENTS

| | | |
|---|---|---|
| 2025145 | 3/1991 | Canada. |
| 2113510 | 7/1994 | Canada. |
| 0130532 | 1/1985 | European Pat. Off.. |
| 0407961 | 1/1991 | European Pat. Off.. |
| 0417680 | 3/1991 | European Pat. Off.. |
| 0609123 | 8/1994 | European Pat. Off.. |
| 2032098 | 1/1971 | Germany. |
| 1307224 | 2/1973 | United Kingdom. |

OTHER PUBLICATIONS

Chemical Abstract, vol. 113, No. 17, Oct. 22, 1990, Columbus, Ohio, US; abstract No. 151815; Morikawa S et al: "Fluorination of perchloroethylene".

*Primary Examiner*—Johann Richter
*Assistant Examiner*—Laura L. Stockton
*Attorney, Agent, or Firm*—Connoly & Hutz

[57] ABSTRACT

The invention relates to a process for preparing pentafluoroethane (R 125) by reacting perchloroethylene with hydrogen fluoride in the gas phase over a chromium-containing catalyst, wherein the catalyst used comprises chromium and magnesium and is obtainable by reacting a water-soluble chromium(III) salt with magnesium hydroxide or magnesium oxide and, if desired, graphite in the presence of water, converting the reaction mixture into a paste, then drying the paste and treating it with hydrogen fluoride at temperatures of from 20° to 500° C., using such amounts of chromium (III) and magnesium salts and, if desired, graphite that the dried paste before treatment with hydrogen fluoride contains from 4.5 to 26% by weight of Cr, expressed as $Cr_2O_3$, and at least 25% by weight of Mg, expressed as MgO, and, if desired, graphite.

13 Claims, No Drawings

PROCESS FOR PREPARING PENTAFLUOROETHANE (R 125)

The present invention relates to a process for preparing pentafluoroethane (R 125) by reacting perchloroethylene ($Cl_2C=CCl_2$) with hydrogen fluoride in the gas phase over a chromium-containing catalyst. R 125, as a chlorine-free compound, does not damage the ozone layer and is therefore suitable as a substitute for CFCs.

Such processes for preparing R 125 are already known. GB-A-1 307 224 describes this reaction using an unsupported chromium oxide catalyst (Table IV, Example 23). However, this process forms as by-product 20% of R 115 ($CF_3CF_2Cl$) which has a high ozone degradation potential (ODP) and therefore has to be very substantially removed from the desired R 125. Since R 115 forms an azeotrope with R 125, its removal is only possible with considerable effort and with loss of part of the R 125. R 115 cannot be recirculated to the process.

US-A-3 258 500 likewise describes the conversion of perchloroethylene to R 125 over a chromium oxide catalyst (Example 17). However, here too the "desired material selectivity", i.e. the selectivity for R 125 and those by-products ($C_2HCl_{1+x}F_{4-x}$, x=0 to 3) which can be recirculated to the process and thus converted into R 125, is too low for an economical process. At 300° C., the desired material selectivity is less than 80% and at 450° C. less than 50%.

When using the catalyst described in EP-A-0 609 123, which contains nickel in addition to chromium, in said reaction, several thousand ppm to 1.4 percent of the olefin trichlorofluoroethylene (R 1111) are formed (page 6, Table 1 and page 7, Table 2). Owing to its toxicity, this has to be removed, which, however, requires considerable effort.

It has now been found that high-purity R 125 is obtained from perchloroethylene and hydrogen fluoride by means of a catalyst prepared in a particular way and comprising chromium and magnesium and, if desired, graphite.

The invention provides a process for preparing pentafluoroethane (R 125) by reacting perchloroethylene with hydrogen fluoride in the gas phase over a chromium-containing catalyst, wherein the catalyst used comprises chromium and magnesium and is obtainable by reacting a water-soluble chromium(III) salt with magnesium hydroxide or magnesium oxide and, if desired, graphite in the presence of water, converting the reaction mixture into a paste, then drying the paste and treating it with hydrogen fluoride at temperatures of from 20° to 500° C., using such amounts of chromium and magnesium salts and, if desired, graphite that the dried paste before treatment with hydrogen fluoride contains from 4.5 to 26% by weight of Cr, expressed as $Cr_2O_3$, and at least 25% by weight of Mg, expressed as MgO, and, if desired, graphite.

Surprisingly, the process of the present invention enables pentafluoroethane to be prepared in high yield. The compounds of the formula $C_2HCl_{1+x}F_{4-x}$, x=0 to 3, i.e. $C_2HClF_4$, $C_2HCl_2F_3$, $C_2HCl_3F_2$ and $C_2HCl_3F$, which are formed as by-products in this process, can be converted into R 125 by recirculation to the reactor; they are therefore hereinafter also referred to (besides R 125 itself) as "desired materials". The process has the great advantage that, apart from these desired materials, no further by-products are formed in significant amounts.

Catalysts which fall under the definition just given have already been described in the literature, but are used there for other reactions:

According to EP-A-0 130 532, a catalyst prepared by reacting 1 mol of a water-soluble chromium(III) salt with at least 1.5 mol, preferably from 12 to 24 mol, of magnesium hydroxide or magnesium oxide is used for the fluorination or dismutation of haloalkanes by means of HF (column 5, lines 4–9, and also the Examples). Here, chlorine is replaced by fluorine in saturated halogenated hydrocarbons. An addition of HF to perchloroethylene and a replacement of all chlorine atoms by fluorine atoms, as occurs in the present process, is neither described nor suggested.

The same catalyst as in EP-A-0 130 532 is used according to EP-A-0 417 680 for reacting 1,1,1-trifluoro-2-chloroethane with HF to give 1,1,1,2-tetrafluoroethane. In this reaction, a chlorine is again replaced by fluorine in a saturated halogenated hydrocarbon.

The same catalyst is used according to EP-A-0 407 961 for preparing 1,1,1-trifluoro-2-chloroethane by reaction of trichloroethylene with HF. Although this is an addition of HF to an unsaturated halogenated hydrocarbon combined with a partial replacement of chlorine by fluorine, only two of the three chlorine atoms present in the starting material are replaced by fluorine atoms. In contrast, in the present process, not only is HF added, but all four chlorine atoms present in the starting material perchloroethylene $Cl_2C=CCl_2$ are replaced by fluorine atoms, so that the chlorine-free fluorinated hydrocarbon pentafluoroethane $CF_3$—$CF_2H$ (R 125) is formed as final product.

The reaction of the present invention proceeds with almost quantitative conversion of the perchloroethylene to give high yields of R 125, and with high selectivity for the desired materials of the process (R 125 and the abovementioned by-products which can be converted by recycling into R 125). In-between work-up of the raw gas, e.g. removal of the HCl formed in the reaction to shift the equilibrium towards R 125, is not necessary. Toxic olefins such as R 1111 (trichlorofluoroethylene) and R 1112a (1,1-dichloro-2,2-difluoroethylene) are formed only in very small amounts in the vicinity of the detection limit.

The catalyst used according to the present invention is obtainable by reacting a water-soluble chromium(III) salt with magnesium hydroxide or magnesium oxide and, if desired, graphite in the presence of water, converting the reaction mixture into a paste, thee drying the paste and treating it with hydrogen fluoride at temperatures of from 20° to 500° C., using such amounts of chromium and magnesium salts and, if desired, graphite that the dried paste before treatment with hydrogen fluoride contains from 4.5 to 26% by weight of Cr, expressed as $Cr_2O_3$, and at least 25% by weight of Mg, expressed as MgO, and, if desired, graphite.

Preference is given to using such amounts of chromium and magnesium salts and, if desired, graphite that the dried paste before treatment with hydrogen fluoride contains from 5.5 to 23% by weight of Cr, expressed as $Cr_2O_3$, and at least 25% by weight of Mg, expressed as MgO, and, if desired, graphite. The proportion of graphite, which is not catalytically active but aids the shaping of the catalyst particles, is preferably from 5 to 40% by weight.

The meanings of the expressions "Cr, expressed as $Cr_2O_3$" and "Mg, expressed as MgO" are clarified by the following specific example of a calculation:

The percentage contents indicated relate to a point in time after drying and before HF treatment of the catalyst. Chromium and magnesium are expressed as $Cr_2O_3$ and MgO so as to eliminate the dependence of the percentage calculation on the anions irrelevant to the reaction present in the chromium and magnesium salts selected in each case.

A catalyst suitable for the process of the present invention is prepared using, for example, 2800 g of $Cr(NO_3)_3$·

9H$_2$O, 2000 g of MgO, 800 g of graphite and 4000 g of water. The indicated amount of chromium salt corresponds, calculated as Cr$_2$O$_3$, to an amount of 531.8 g. The chromium content of this catalyst, expressed as Cr$_2$O$_3$, is calculated as folllows: 531.8 g (Cr$_2$O$_3$)/(531.8 g (Cr$_2$O$_3$) +2000 g (MgO) +800 g (graphite))=531.8 g/3331.8 g=16% by weight. The magnesium content, expressed as MgO, is 2000 g/3331.8 g=60% by weight, and the graphite content is 800 g/3331.8 g=24% by weight.

Chromium(III) compounds used can be either anhydrous or, preferably, hydrated salts of trivalent chromium which are readily available and obtainable commercially. It is possible to use, for example, chromium(III) sulfate and chromium(III) fluoride, but preferably chromium(III) chloride and chromium(III) nitrate.

The magnesium oxide used must not have been ignited, but must still be able to react with weakly acid compounds. Since the preparation of the catalyst does not involve a washing procedure, the molar ratio of magnesium/chromium in the starting components is the same as in the finished catalyst.

The amount of water used is not critical for the preparation of the catalyst; however, the amount of water has to be sufficient for the mass to be processable, at least by means of a kneader. However, the higher the amount of water used, the more water has to be evaporated during drying.

To prepare the catalysts, it is possible, for example, to add the chromium compound as aqueous solution to dry magnesium oxide or hydroxide and to knead the resulting mixture, if desired together with graphite, to give a paste.

As an alternative, it is possible to mix the initially charged magnesium oxide into a paste with water, add the chromium compound dry, if desired add graphite, and knead the reaction mixture.

The kneading is advantageously carried out using machines which are customarily used in process technology for mixing paste-like materials, e.g. vertical kneaders or duplex kneaders.

In the preparation of the catalysts used according to the present invention, the paste obtained is dried without washing. It is directly suitable for the production of shaped bodies. An advantage is that the shaped bodies can be produced using conventional processing methods such as pelleting, extruding or granulation.

After shaping, the shaped bodies are dried, giving catalyst particles which are very stable mechanically. Drying can be carried out either at room temperature or at elevated temperature. Advantageously, a drying temperature of from 50° to 150° C., preferably from 70° to 120° C., is selected so as to keep the drying time short. Drying can be carried out either under atmospheric pressure or under reduced pressure.

Drying should not be carried out at temperatures above 400° C., since otherwise the chromium oxide can lose its reactivity towards hydrogen fluoride.

The treatment of the catalyst with hydrogen fluoride before use is advantageously carried out at temperatures of from 150° to 500° C., preferably from 150° to 450° C. The amount of hydrogen fluoride used is not critical. The fluorination time can be selected within wide limits; preference is given to from 0.5 to 10 hours. To quickly remove the water formed and to avoid undesired temperature peaks, HF is preferably diluted with an inert gas (e.g. N$_2$ or air).

If the catalyst activity drops later on, this can be completely restored by regeneration using suitable agents (oxidants such as oxygen mixed with a suitable diluent such as nitrogen or HF). This regeneration can be carried out a plurality of times without noticeable damage to the catalyst occurring.

The process of the present invention can be carried out, for example, in such a way that the starting materials perchloroethylene and hydrogen fluoride are continuously supplied to a vaporizer of stainless steel or nickel. The vaporization temperature has to be sufficient to vaporize the entire reaction mixture, but is otherwise not critical for the course of the reaction. The gaseous starting materials go through a heated path into a gas mixer and then into the reactor. The gas mixer can also be located in the lower part of the reactor containing the bed of catalyst.

The process of the present invention can be carried out in a single reactor or else in a plurality of reactors connected in series (cascade). When using a cascade, the hydrogen chloride formed in the reaction can be separated off after passing through the last reactor (single-stage procedure) or part of the hydrogen chloride is separated off after one or more of the reactors preceding the last one and the remainder is separated off after the last reactor (multistage procedure).

The reactor or the reactors are made of a resistant material such as stainless steel, nickel or Hastelloy. The reactor shape can be selected from among various industrial embodiments such as a tube reactor, annular gap reactor or shaft reactor.

The reaction zone is maintained at a temperature of from 150° to 450° C., preferably from 180° to 370° C., in particular from 200° to 350° C., by means of external heating. When using a cascade, it is useful to select, from the ranges indicated, a temperature in the first and last reactors which is lower than that in the reactor(s) located in between.

To achieve as complete as possible a conversion of the perchloroethylene, the hydrogen fluoride is preferably used in excess. The molar ration HF:perchloroethylene is preferably from 3:1 to 10:1, in particular from 4:1 to 8:1.

The gas-phase reaction of the present invention is particularly effective under superatmospheric pressure, since the high conversion is then maintained over a longer period of time. During the reaction, the pressure is set by means of a regulating valve to from 1 to 26 bar, preferably from 2 to 17 bar, particularly preferably from 4 to 10 bar. In continuous operation, the work-up of the reaction mixture advantageously comprises separating off the hydrogen chloride, the target product R 125 and the highly fluorinated by-products formed during passage through the reactor and also recirculating the tail gas, which is enriched with fresh hydrogen fluoride and perchloroethylene, into the reaction section. Technical-grade starting materials are used. In particular, the residual amount of water is advantageously minimized. The starting compounds can be prepared in a simple manner by known methods.

The process of the present invention is illustrated by the following examples. Percentages given for the GC analysis are percentages by area.

EXAMPLES

Cr(NO$_3$)$_3$. 9H$_2$O was dissolved in water. This solution was added to a mixture of magnesium oxide and graphite and the paste-like mass thus formed was intimately kneaded. The paste-like product was subsequently granulated and dried for 20 hours at 100° C. The amounts of material used in the various catalyst batches are shown in Table 1. The dried catalysts A to E were activated before carrying out the respective test in the reaction tube described in the comparative example by treatment with a HF/nitrogen mixture at temperatures between 200° and 500° C. This treatment took from 6 to 15 hours.

TABLE 1

| Catalyst | A | B | C | D | E |
|---|---|---|---|---|---|
| Cr content (% by weight) expressed as $Cr_2O_3$ | 4.3 | 5.1 | 16.0 | 23.3 | 26.3 |
| Mg content (% by weight) expressed as MgO | 82.4 | 67.8 | 60.0 | 53.7 | 51.6 |
| Graphite content (% by weight) | 13.2 | 27.1 | 24.0 | 23.0 | 22.1 |
| Amounts used [g]: | | | | | |
| $Cr(NO_3)_3 \cdot 9H_2O$ | 310 | 400 | 2800 | 800 | 940 |
| MgO | 1120 | 1000 | 2000 | 350 | 350 |
| Graphite | 180 | 400 | 800 | 150 | 150 |
| Water | 450 | 600 | 1200 | 1200 | 1500 |

COMPARATIVE EXAMPLE

Perchloroethylene and hydrogen fluoride were mixed in the molar ratio indicated (Table 2), fed via heated lines to a vaporizer and passed in the gaseous state over the bed of catalyst A in a tube reactor of nickel ($\phi$=42 mm). The amount of unactivated catalyst charged was 0.5 l bed volume prior to activation. The reactor was electrically heated. The reaction temperature indicated (Table 2) is the average temperature in the interior of the catalyst bed. The gaseous products leaving the reactor were passed through a water scrub. After drying the product gas stream with $CaCl_2$, a sample was taken. The samples were analyzed by gas chromatography. The composition found for the product gas stream is shown in Table 2.

EXAMPLES 1 to 5

The catalysts B, C, D, E were tested exactly like catalyst A under the conditions shown in Table 2. The results are shown in the same table. Catalyst C was tested once at 320° C. (Example 2) and once at 295° C. (Example 5).

| Example No. | Comparative Example | 1 | 2 | 3 | 4 | 5 |
|---|---|---|---|---|---|---|
| Catalyst | A | B | C | D | E | C |
| Cr content, expressed as $Cr_2O_3$ [% by weight] | 4.3 | 5.1 | 16.0 | 23.3 | 26.3 | 16.0 |
| Molar ratio HF/perchloroethylene | 5.1/1 | 5.0/1 | 5.2/1 | 5.4/1 | 5.3/1 | 5.1/1 |
| Pressure [bar abs.] | 1 | 1 | 1 | 1 | 1 | 1 |
| Residence time [s] | 10 | 11 | 10 | 9 | 10 | 10 |
| Reaction temperature [°C.] | 320 | 320 | 320 | 320 | 320 | 295 |
| Conversion of perchloroethylene [%] | 38.7 | 75.9 | 93.0 | 77.6 | 60.1 | 89.0 |
| Selectivity for desired material [%] | 97.4 | 97.5 | 97.5 | 97.2 | 95.0 | 97.9 |
| Products obtained [%] R 125 | 8.2 | 20.4 | 34.4 | 27.0 | 20.1 | 23.4 |
| R 124s | 16.4 | 27.7 | 18.4 | 20.1 | 17.0 | 25.4 |
| R 123s | 12.5 | 25.0 | 36.2 | 27.9 | 19.6 | 35.3 |
| R 122s | 0.6 | 0.9 | 1.7 | 0.4 | 0.4 | 3.0 |
| R 121s | Traces | Traces | Traces | Traces | Traces | Traces |
| R 1111 | 400 ppm | 200 ppm | 200 ppm | 300 ppm | 300 ppm | 150 ppm |
| R 1112a | 700 ppm | 60 ppm | 100 ppm | 180 ppm | 180 ppm | 80 ppm |
| $\Sigma_R$ 130 compounds | 0.4 | 0.9 | 1.0 | 1.1 | 1.4 | 0.6 |
| $\Sigma_R$ 110 compounds | 0.4 | 0.9 | 1.0 | 1.0 | 1.4 | 0.6 | s = Sum for all structural isomers occurring which have the same empirical formula (Example: R 123s = R 123, R 123a and R 123b)
$\Sigma_R$ 110 compounds = Sum for all compounds assigned a number combination between 110 and 120 (R 111, R 112, R 113, R 114 and their structural isomers, and also R 115 and R 116). This rule is to be used analogously for the R 130 series
Selectivity for desired material = selectivity to give R 125 + R 124s + R 123s + R 122s + R 121s

We claim:

1. A process for preparing pentafluoroethane by reacting perchloroethylene with hydrogen fluoride in the gas phase over a catalyst containing chromium and magnesium and, optionally, graphite, said catalyst being prepared by
    (a) reacting a water-soluble chromium (III) salt with magnesium hydroxide or magnesium oxide in the presence of water and, optionally, graphite,
    (b) converting the resulting reaction mixture into a paste, then
    (c) drying the paste and treating it with hydrogen fluoride at a temperature of from 20° to 500° C.,
    using in step (a) the chromium (III) and magnesium compounds and, optionally, graphite, in such amounts that, if the chromium and magnesium are present as $Cr_2O_3$ and MgO, the dried paste would contain from 4.5 to 26% by weight of $Cr_2O_3$ and at least 25% by weight of MgO.

2. The process as claimed in claim 1, using in step (a) the chromium (III) and magnesium compounds, and, optionally, graphite, in such amounts that, if the chromium and magnesium are present as $Cr_2O_3$ and MgO, the dried paste would contain from 5.5 to 23% by weight of $Cr_2O_3$.

3. The process as claimed in claim 1, using in step (a) the chromium (III) and magnesium compounds and graphite in such amounts, that, if the chromium and magnesium are present as $Cr_2O_3$ and MgO, the dried paste would contain from 5 to 40% by weight of graphite.

4. The process as claimed in claim 1, wherein the reaction of perchloroethylene with hydrogen fluoride is carried out at a temperature of from 150° to 450° C.

5. The process as claimed in claim 1, wherein the reaction of perchloroethylene with hydrogen fluoride is carried out at a pressure of from 2 to 17 bar.

6. The process as claimed in claim 1, wherein the reaction of perchloroethylene with hydrogen fluoride is carried out at a pressure of from 4 to 10 bar.

7. The process as claimed in claim 1, wherein the reaction of perchloroethylene with hydrogen fluoride is carried out at a molar ratio HF:perchloroethylene of from 3:1 to 10:1.

8. A process for preparing pentafluoroethane by reacting perchloroethylene with hydrogen fluoride in the gas phase over a catalyst containing chromium and magnesium and, optionally, graphite, in such amounts that, if the chromium and magnesium are present as $Cr_2O_3$ and MgO, the catalyst would contain from 4.5 to 26% by weight of $Cr_2O_3$ and at least 25% by weight of MgO.

9. The process as claimed in claim 8, wherein the catalyst contains 5.5 to 23% by weight of $Cr_2O_3$, and at least 25% by weight of MgO and, optionally, graphite.

10. The process as claimed in claim 8, wherein the reaction of perchloroethylene with hydrogen fluoride is carried out at a temperature of from 150° to 450° C.

11. The process as claimed in claim 8, wherein the reaction of perchloroethylene with hydrogen fluoride is carried out at a pressure of from 2 to 17 bar.

12. The process as claimed in claim 8, wherein the reaction of perchloroethylene with hydrogen fluoride is carried out at a pressure of from 4 to 10 bar.

13. The process as claimed in claim 8, wherein the reaction of perchloroethylene with hydrogen fluoride is carried out at a molar ratio HF:perchloroethylene of from 3:1 to 10:1.

* * * * *